(12) United States Patent
Moheno

(10) Patent No.: US 6,358,953 B1
(45) Date of Patent: Mar. 19, 2002

(54) PTERIN ANTINEOPLASTIC AGENTS

(75) Inventor: Phillip B. B. Moheno, 603 Colima St., La Jolla, CA (US) 92037

(73) Assignee: Phillip B. B. Moheno, La Jolla, CA (US)

( * ) Notice: Subject to any disclaimer, the term of this patent is extended or adjusted under 35 U.S.C. 154(b) by 0 days.

(21) Appl. No.: 09/422,846

(22) Filed: Oct. 21, 1999

Related U.S. Application Data
(60) Provisional application No. 60/135,834, filed on May 24, 1999, and provisional application No. 60/105,172, filed on Oct. 22, 1998.

(51) Int. Cl.⁷ .............................. C07F 1/08; A61K 33/34
(52) U.S. Cl. ...................... 514/249; 544/225; 544/258; 544/261
(58) Field of Search ................................. 544/225, 258, 544/261; 514/249

(56) References Cited

U.S. PATENT DOCUMENTS

| 2,688,018 A | 8/1954 | Cosulich et al. |
| 3,635,978 A | 1/1972 | Hamisch |
| 5,534,514 A | 7/1996 | Moheno |

OTHER PUBLICATIONS

Kucharska Talanta 44 (1997) 85–96.*
Burgmayer ACS Symposium Series 535p114–129, Aug. 1992.*

* cited by examiner

*Primary Examiner*—Robert Gerstl
(74) *Attorney, Agent, or Firm*—Brobeck, Phleger & Harrison, LLP

(57) ABSTRACT

Disclosed are novel metal pterin and pterin analog complexes and compositions useful as antineoplastic and antiviral agents.

35 Claims, 2 Drawing Sheets

PTERIN ANTINEOPLASTIC AGENTS

RELATED APPLICATION

Figure 1:
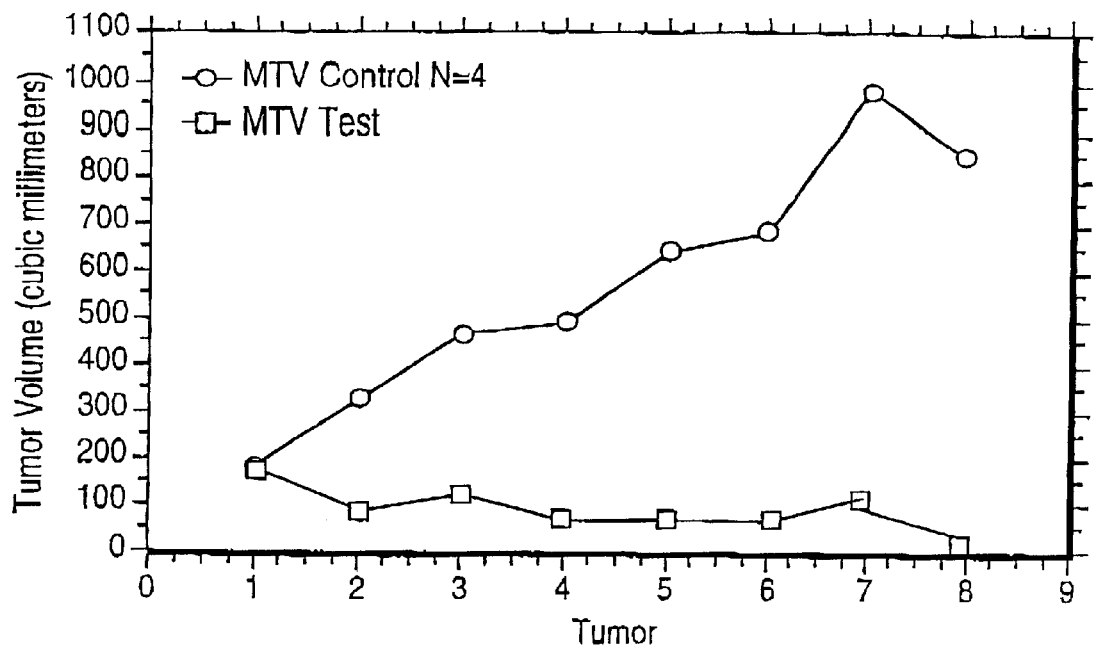
Figure 2:
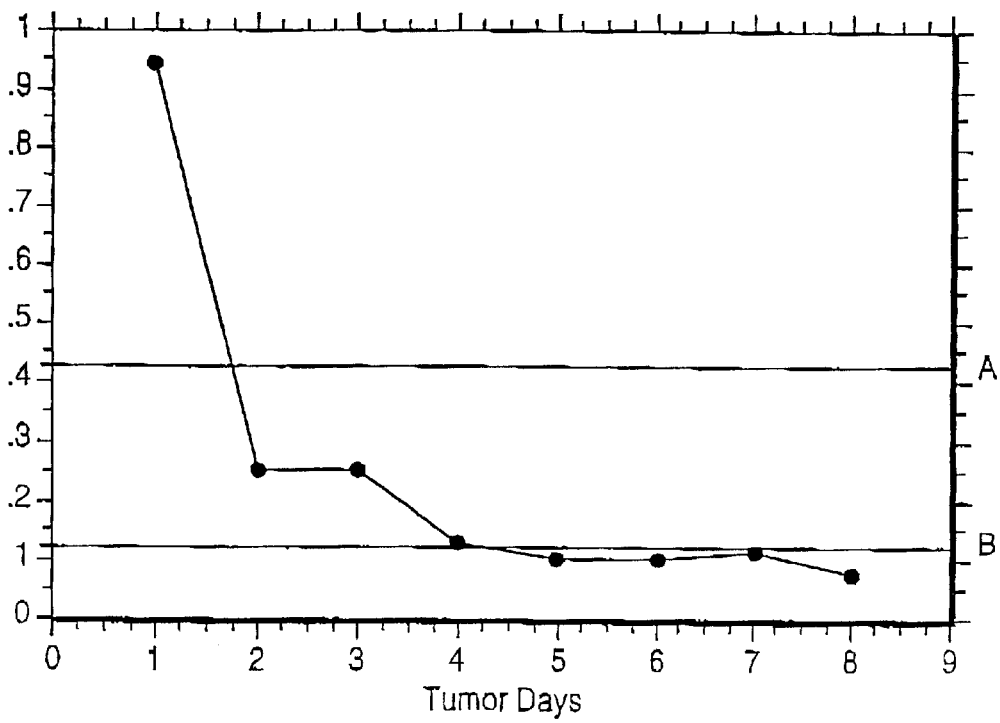

This application is a continuation-in-part of provisional application Ser. No. 60/135,834 filed May 24, 1999, which is a continuation-in-part of provisional application Ser. No. 60/105,172 filed Oct. 22, 1998, which are incorporated by reference herein in their entirety.

FIELD OF THE INVENTION

This invention relates to novel pterin and pterin analog metal complexes that possess potent antineoplastic activity. This invention also relates to the preparation and use of these complexes in the treatment and prevention of cancer and viral infections.

BACKGROUND AND INTRODUCTION TO THE INVENTION

Hundreds of thousands of people die every year from cancer and for decades scientists have been searching for effective treatments. There are a wide variety of antineoplastic agents available. These agents are generally classified as alkylating agents, DNA binders, antimetabolites, and mitotic inhibitors.

While none have become an FDA approved cancer drug, it was known that several pteridine derivatives possessed some antineoplastic activity. For example, U.S. Pat. No. 5,534,514 teaches that xanthopterin, isoxanthopterin, and neopterin derivatives have antineoplastic activity. Also, 10-deazaminopterin, and 10-ethyl-10-deazaminopterin could be used in the treatment of leukemia according to U.S. Pat. Nos. 4,393,064 and 4,753,939, respectively. Pterin suspensions were tested by the NIH but showed no significant antineoplastic activity. None of these references disclose metal complexes of pterin or pterin analogs to treat cancer.

Metal complexes with specific ligands have been used successfully as antitumor agents. Cisplatin and carboplatin are two of such compounds.

Although there are a number of anticancer agents on the market, there will always be certain cancers which are resistant. Thus, there is a need for new antineoplastic agents.

SUMMARY OF THE INVENTION

The present invention is directed to novel metal pterin and pterin analog complexes of the formula I $$(MX_a)_y(Pterins)_z \quad (I)$$

wherein

M is a bivalent metal ion selected from the group consisting of $Ca^{2+}$, $Cu^{2+}$, $Mg^{2+}$, $V^{2+}$, $Cr^{2+}$, $Mn^{2+}$, $Fe^{2+}$, $Co^{2+}$, $Zn^{2+}$, $Mo^{2+}$, $Sr^{2+}$, $Ba^{2+}$, $Ra^{2+}$, $Ru^{2+}$, $Rh^{2+}$, $Pd^{2+}$, $Cd^{2+}$, $Sn^{2+}$, $W^{2+}$, $Re^{2+}$, $Os^{2+}$, $Ir^{2+}$, $Pt^{2+}$, $Si^{2+}$, and $Sm^{2+}$;

X is an anion of an acid and has a charge of −1 or −2 when ionized;

a is an integer of from 1 to 2;

y is an integer of from 1 to 6; and z is an integer of from 1 to 6.

Also within the scope of the invention are suspensions prepared from Pterins and metal salts. Such suspensions are administered as antineoplastic and/or antiviral agents.

Definitions

"Pterins" refers to the following compounds which can exist as the tautomers

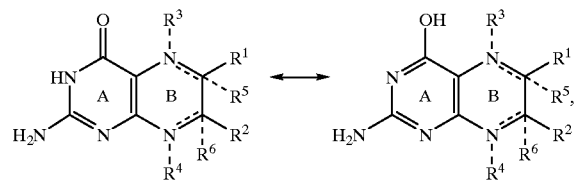

wherein $R^1$ and $R^2$ are independently selected from the group consisting of hydrogen, alkyl, perhaloalkyl, carboxyl, amido, carboxamido, oxo, carboxy esters, amino, halogen, haloalkyl, hydroxy, alkoxy, azido, acylalkyl, hydroxyalkyl, —C(O)H, aryl, alicyclic, aralkyl, thioalkyl, sulfhydryl (—SH), sulfonyl ($SO^{2-}_3$), —CN, perhaloalkoxy, and acyl;

$R^5$ and $R^6$ are independently selected from the group consisting of hydrogen, alkyl, perhaloalkyl, carboxyl, amido, carboxamido, oxo, carboxy esters, amino, halogen, haloalkyl, hydroxy, alkoxy, azido, acylalkyl, hydroxyalkyl, —C(O)H, aryl, alicyclic, aralkyl, thioalkyl, sulfhydryl (—SH), sulfonyl ($SO^{2-}_3$), —CN, perhaloalkoxy, acyl, and null;

$R^3$ and $R^4$ are independently selected from the group consisting of —H, alkyl, —C(O)H, acyl, hydroxyalkyl, aryl, alkylaryl, hydroxy, oxo, acylalkyl, haloalkyl, perhaloalkyl, haloaryl, carboxyl, and null.

The dotted lines in the above structures represent optional bonds. The nitrogens in the B-ring can be neutral or positively charged. Thus, "Pterins" refers to both Pterin and pterin analogs including, but not limited to pterin, xanthopterin, and isoxanthopterin.

"Suspension" refers to the state of a substance when its particles are mixed but undissolved in a fluid or solid.

"RCOOH" refers to carboxylic acids, where R is alkyl, aryl, or aralkyl. Suitable anion carboxylic acids include $CH_3COO^-$, and phenyl-$COO^-$.

"Alkyl" refers to saturated and unsaturated aliphatic groups including straight-chain, branched chain, and cyclic groups. Alkyl groups may be optionally substituted. Alkyl groups may contain double or triple bonds. Suitable alkyl groups include methyl.

"Aryl" refers to aromatic groups which have 5–14 ring atoms and at least one ring having a conjugated pi electron system and includes carbocyclic aryl, heterocyclic aryl, and biaryl groups, which may be optionally substituted. Suitable aryl groups include phenyl.

Carbocyclic aryl groups are groups wherein the ring atoms on the aromatic ring are carbon atoms. Carbocyclic aryl groups include monocyclic and carbocyclic aryl groups and polycyclic or fused compounds such as optionally substituted naphthyl groups.

Heterocyclic aryl or heteroaryl groups are groups having from 1 to 4 heteroatoms as ring atoms in the aromatic ring and the remainder of the ring atoms being carbon atoms. Suitable heteroatoms include oxygen, sulfur, and nitrogen. Suitable heteroaryl groups include furanyl, thienyl, pyridyl, pyrrolyl, N-lower alkyl pyrrolyl, pyridyl-N-oxide, pyrimidyl, pyrazinyl, imidazolyl, and the like, all optionally substituted.

The term "biaryl" represents aryl groups containing more than one aromatic ring including both fused ring systems and aryl groups substituted with other aryl groups. Such groups may be optionally substituted. Suitable biaryl groups include naphthyl and biphenyl.

The term "alicyclic" means compounds which combine the properties of aliphatic and cyclic compounds. Such cyclic compounds include but are not limited to, aromatic, cycloalkyl and bridged cycloalkyl compounds. The cyclic compound includes heterocycles. Cyclohexenylethyl and cyclohexylethyl are suitable alicyclic groups. Such groups may be optionally substituted.

The term "optionally substituted" or "substituted" includes groups substituted by one to four substituents, independently selected from lower alkyl, lower aryl, lower aralkyl, lower alicyclic, hydroxy, lower alkoxy, lower aryloxy, perhaloalkoxy, aralkoxy, halo, azido, amino, acyl, lower alkylthio, oxo, acylalkyl, carboxy esters, carboxyl, carboxamido, nitro, acyloxy, alkylaryl, alkoxyaryl, phosphono, sulfonyl, hydroxyalkyl, haloalkyl, cyano, lower alkoxyalkyl, lower perhaloalkyl, and aralkyloxyalkyl.

The term "aralkyl" refers to an alkyl group substituted with an aryl group. Suitable aralkyl groups include benzyl, picolyl, and the like, and may be optionally substituted. The term "-aralkyl-" refers to a divalent group -aryl-alkylene-.

The term "lower" referred to herein in connection with organic radicals or compounds respectively defines such as with up to and including 10, preferably up to and including 6, and advantageously one to four carbon atoms. Such groups may be straight chain, branched, or cyclic.

The term "acyl" refers to —C(O)R where R is H, alkyl, and aryl.

The term "carboxy esters" refers to —C(O)OR where R is alkyl, aryl, aralkyl, and alicyclic, all optionally substituted.

The term "carboxyl" refers to —C(O)OH.

The term "oxo" refers to =O in an alkyl group.

The term "amino" refers to —NRR' where R and R' are independently selected from hydrogen, alkyl, aryl, aralkyl and alicyclic, all except H are optionally substituted; and R and $R^1$ can form a cyclic ring system.

The term "halogen" or "halo" refers to —F, —Cl, —Br and —I.

The term "cyclic alkyl" or "cycloalkyl" refers to alkyl groups that are cyclic. Suitable cyclic groups include norbornyl and cyclopropyl. Such groups may be substituted.

The term "heterocyclic" and "heterocyclic alkyl" refer to cyclic groups containing at least one heteroatom. Suitable heteroatoms include oxygen, sulfur, and nitrogen. Heterocyclic groups may be attached through a nitrogen or through a carbon atom in the ring. Suitable heterocyclic groups include pyrrolidinyl, morpholino, morpholinoethyl, and pyridyl.

The term "phosphono" refers to —$PO_3R_2$, where R is selected from the group consisting of —H, alkyl, aryl, aralkyl, and alicyclic.

The term "sulphonyl" or "sulfonyl" refers to —$SO_3R$, where R is H, alkyl, aryl, aralkyl, and alicyclic.

The term "alkylene" refers to a divalent straight chain, branched chain or cyclic saturated aliphatic group.

The term "aralkyloxyalkyl-" refers to the group aryl-alk-O-alk- wherein "alk" is an alkylene group. "Lower aralkyloxyalkyl-" refers to such groups where the alkylene groups are lower alkylene.

The term "-alkoxy-" or "-alkyloxy-" refers to the group -alk-O- wherein "alk" is an alkylene group.

The term "alkoxy-" refers to the group alkyl-O—.

The term "-alkoxyalkyl-" or "-alkyloxyalkyl-" refer to the group -alk-O-alk-wherein each "alk" is an independently selected alkylene group. In "lower -alkoxyalkyl-", each alkylene is lower alkylene.

The terms "alkylthio-" and "-alkylthio-" refer to the groups alkyl-S-, and -alk-S—, respectively, wherein "alk" is alkylene group.

The term "-alkylthioalkyl-" refers to the group -alk-S-alk- wherein each "alk" is an independently selected alkylene group. In "lower -alkylthioalkyl-" each alkylene is lower alkylene.

The terms "amido" or "carboxamido" refer to $NR_2$—C(O)— and RC(O)—$NR^1$—, where R and $R^1$ include H, alkyl, aryl, aralkyl, and alicyclic.

The term "perhalo" refers to groups wherein every C—H bond has been replaced with a C-halo bond on an aliphatic or aryl group. Suitable perhaloalkyl groups include —$CF_3$ and —$CFCl_2$.

The term "pharmaceutically acceptable salt" includes salts of compounds of formula I and their prodrugs derived from the combination of a compound of this invention and an organic or inorganic acid or base.

The term "prodrug" as used herein refers to any compound that when administered to a biological system generates the "drug" substance either as a result of spontaneous chemical reaction(s) or by enzyme catalyzed or metabolic reaction(s). Prodrugs are formed using groups attached to functionality, e.g. HO—, HS—, HOOC—, $R_2N$—, associated with the Pterins, that cleave in vivo. Prodrugs include but are not limited to carboxylate esters where the group is alkyl, aryl, aralkyl, acyloxyalkyl, alkoxycarbonyloxyalkyl as well as esters of hydroxyl, thiol and amines where the group attached is an acyl group, an alkoxycarbonyl, aminocarbonyl, phosphate or sulfate. The groups illustrated are exemplary, not exhaustive, and one skilled in the art could prepare other known varieties of prodrugs. Such prodrugs of the compounds of formula I, fall within the scope of the present invention.

DETAILED DESCRIPTION OF THE INVENTION

The inventor has discovered that suspensions prepared from Pterins and salts of bivalent cations possess remarkable antineoplastic activity. It is believed that compounds of the general formula of $(MX_a)_y(Pterins)_z$ possess highly significant antineoplastic efficacy in mammals, where M represents a metal ion selected from the group consisting of $Ca^{2+}$, $Cu^{2+}$, $Mg^{2+}$, $V^{2+}$, $Cr^{2+}$, $Mn^{2+}$, $Fe^{2+}$, $Co^{2+}$, $Zn^{2+}$, $Mo^{2+}$, $Sr^{2+}$, $Ba^{2+}$, $Ra^{2+}$, $Ru^{2+}$, $Rh^{2+}$, $Pd^{2+}$, C $Sn^{2+}$, $W^{2+}$, $Re^{2+}$, $Os^{2+}$, $Ir^{2+}$, $Pt^{2+}$, $Si^{2+}$, and $Sm^{2+}$; X is an anion of an acid and has a charge of −1 or −2 when ionized; a is an integer of from 1 to 2; and y and z are independently an integer from 1 to 6; with the provisos that:

a) when M is $Cu^{2+}$, then Pterin is not pterin, or 6-carboxy pterin;

b) when M is $Ca^{2+}$, then Pterin is not xanthopterin, isoxanthopterin, or neopterin; and c) when M is $Zn^{2+}$, then Pterin is not pterin.

Scheme One below shows an example of the kind of structures thought to be formed by these compounds in aqueous solution, where a=2, y=1, and z=4. It is thought that there is hydrogen bonding between the Pterins-ligand and another Pterins compound. Such hydrogen bonding is depicted in Scheme Two.

Scheme One

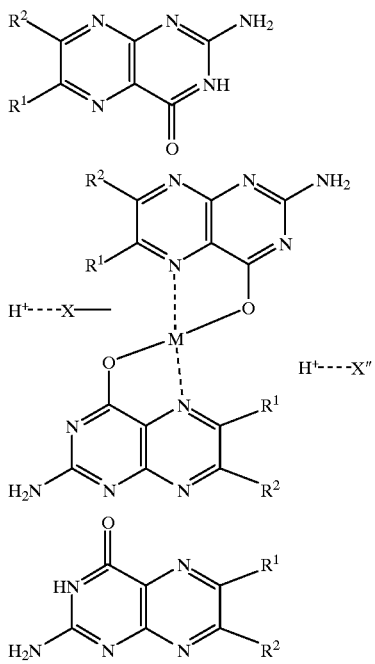

$(MX_2)(pterin)_4$ Metal Ion-Pterin Complex in Solution (Example)

It is believed that $(MX_a)_y(Pterins)_z$ compounds arranged as shown in Schemes Two and Three for $R^1$, $R^2$=H; $R^5$, $R^6$=null; and $R^3$, $R^4$=null, intercalate into the cellular DNA of tumor cells and suppress the expression of those genes necessary for cellular division and growth. Working in synergy with this mechanism, $(MX_a)_y(Pterins)_z$ compounds may suppress the humoral cells of the mammal's immune system, also via a DNA intercalating mechanism, thereby potentiating the killer cells of the immune system against the tumor cells. The suppression of the humoral system inhibits the production of antibodies which can coat the outer surfaces of tumor cells and block the access of killer cells trying to destroy them.

Scheme Two

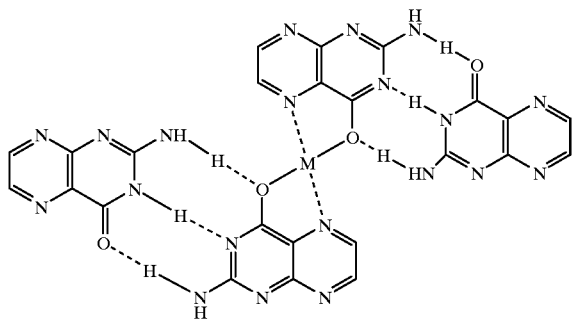

Scheme Three

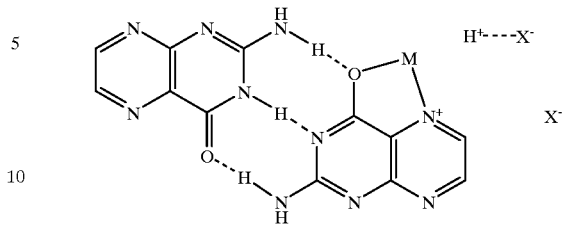

It is thought the metal Pterins compositions of the present invention will be useful in the treatment and prevention of animal neoplasms and viral infections.

Preferred Compounds and Compositions

Suitable alkyl groups include groups having from 1 to about 20 carbon atoms. Suitable aryl groups include groups having from 1 to about 20 carbon atoms. Suitable aralkyl groups include groups having from 2 to about 21 carbon atoms. Suitable acyloxy groups include groups having from 1 to about 20 carbon atoms. Suitable alkylene groups include groups having from 1 to about 20 carbon atoms. Suitable alicyclic groups include groups having 3 to about 20 carbon atoms. Suitable heteroaryl groups include groups having from 1 to about 20 carbon atoms and from 1 to 4 heteroatoms, preferably independently selected from nitrogen, oxygen, phosphorous, and sulfur. Suitable heteroalicyclic groups include groups having from 2 to about twenty carbon atoms and from 1 to 5 heteroatoms, preferably independently selected from nitrogen, oxygen, and sulfur.

Preferred Pterins include Pterin, 6-Formylpterin, 7-Formylpterin, 6-Hydroxymethylpterin, 7-Hydroxymethylpterin, 6-Methylpterin, 7-Methylpterin, 6,7-Dimethylpterin, Pterin-6-carboxylic acid, Pterin-7-carboxylic acid, Xanthopterin, and Isoxanthopterin. More preferred are Pterin, 6-Formylpterin, 7-Formylpterin, 6-Hydroxymethylpterin, 7-Hydroxymethylpterin, 6-methylpterin, 7-Methylpterin, 6,7-Dimethylpterin, Pterin-6-carboxylic acid, and Pterin-7-carboxylic acid. Especially preferred is Pterin.

Preferred compositions are prepared using a molar ratio of Pterins: salt of a bivalent cation of from about 1:1 to about 6:1. More preferred is a ratio of from about 1:1 to about 4:1. Most preferred is a ratio of from about 2:1 to about 4:1. Especially preferred is a ratio of about 4:1.

These compositions can be prepared by combining a solution or suspension of Pterins with a solution or suspension made from the salt of the bivalent cation. The compositions can also be prepared by mixing Pterins and a salt of a bivalent cation with a suitable solvent to form a solution or suspension.

Preferred solvents are polar and include, but are not limited to water, saline, aqueous buffer solutions, DMSO, and lower alcohols such as ethanol and isopropanol. More preferred is water.

Preferred salts of bivalent cations include $CaCl_2$, and $CuCl_2$. These may be in the form of hydration complexes, e.g. $CaCl_2.2H_2O$.

Preferred compounds include Pterins where $R^1$ and $R^2$ are independently selected from the group consisting of —H, methyl, —C(O)H, —$CH_2OH$, —COOH, =O and —Cl. More preferred is —H.

Preferred compounds where $R^5$ and $R^6$ are null.

Preferred compounds include Pterins where $R^3$ and $R^4$ are independently H or null.

Preferred X groups include F⁻, Cl⁻, Br⁻, I⁻, RCOO⁻, $CO_3^{2-}$, $HPO_3^{2-}$, $SO_4^{2-}$, and $SO_3^-$. More preferred are F⁻, Cl⁻, and Br⁻.

Preferred M ions include $Ca^{2+}$, $Cu^{2+}$, $Mg^{2+}$, $V^{2+}$, $Cr^{2+}$, $Mn^{2+}$, $Fe^{2+}$, $Co^{2+}$, $Mo^{2+}$, $Si^{2+}$, and $Zn^{2+}$. More preferred is $Ca^{2+}$ and $Cu^{2+}$. Especially preferred is $Ca^{2+}$. In another aspect $Ca^{2+}$, $Cu^{2+}$, and $Zn^{2+}$ are preferred. In another aspect, the preferred M ions include $Sr^{2+}$, $Ba^{2+}$, $Ra^{2+}$, $RU^{2+}$, $Rh^{2+}$, $W^{2+}$, $Re^{2+}$, $Os^{2+}$, $Ir^{2+}$, $Pt^{2+}$, $Pd^{2+}$, $Cd^{2+}$, $Sn^{2+}$, and $Sm^{2+}$.

In one preferred aspect, the composition is made from Pterins, $CaCl_2$ or $CuCl_2$, water, and optionally excipients in a molar ratio of Pterin: salt or pterin analog: salt of approximately 4:1.

Preferably a is the integer 2.

Preferably y is an integer from 1 to 4. More preferred is 1 or 2. Most preferred is 1.

Preferably z is an integer from 1 to 4. More preferred is 2 to 4. Most preferred is 4.

In one preferred aspect M is $Ca^{2+}$ or $Cu^{2+}$, X is F⁻, Cl⁻ or Br⁻, a is 2, x is 1, and z is 2 or 4.

The following compounds are preferred pterins for practicing in the present invention:

|  | R¹ | R² | R³ | R⁴ | R⁵ | R⁶ |
|---|---|---|---|---|---|---|
| 6-Formylpterin | —C(O)H | H | — | — | — | — |
| 7-Formylpterin | H | —C(O)H | — | — | — | — |
| 6-Hydroxymethylpterin | —CH₂OH | H | — | — | — | — |
| 7-Hydroxymethylpterin | H | —CH₂OH | — | — | — | — |
| 6-Methylpterin | —CH₃ | H | — | — | — | — |
| 7-Methylpterin | H | —CH₃ | — | — | — | — |
| 6,7-Dimethylpterin | CH₃ | —CH₃ | — | — | — | — |
| Pterin-6-carboxylic acid | —COOH | H | — | — | — | — |
| Pterin-7-carboxylic acid | H | —COOH | — | — | — | — |
| Xanthopterin | =O | H | H | — | — | — |
| Isoxanthopterin | H | =O | — | H | — | — |
| Pterin | H | H | — | — | — | — |

Pterin Analogs

As discussed, pterin analogs may also possess the same beneficial characteristics of pterin discussed herein. These analogs include those optionally and independently substituted at N-5 and N-8, and those optionally and independently mono- or bi-substituted at C-6 and C-7 in the basic pterin structure illustrated below. This list is provided for exemplary purposes only and should not be construed as being limiting. Many other pterin analogs are known or would be apparent to those of ordinary skill in the art and such pterin analogs are also contemplated as being within the scope of this invention. Similarly, pterin analogs yet to be discovered but which would also be apparent to one of ordinary skill in the art as being useful in the present invention are also contemplated as being within the scope of the present invention.

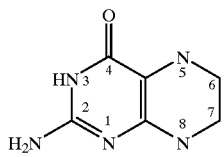

The synthesis of pterin and pterin analogs is well known. Below is given a partial summary of references to procedures which have been developed to synthesize them.

| N-5 | C-6 | C-7 | N-8 |
|---|---|---|---|
| Purmann, R. Liebigs Ann. Chem. 548, 284–92 (1941). | | | |
| H | O | COOH | — |
| — | COOH | O | H |
| H | O | H | — |
| H | O | H | H |
| — | H | O | H |
| Pfleiderer, W. & Rukwied, M. Chem. Ber. 94, 1–12 (1961). | | | |
| — | H | H | CH₃ |
| — | CH₃ | H | CH₃ |
| — | H | Cl, OCH₃ | — |
| Schmid, H. et al.; Chem Ber. 106, 1957–75 (1973). | | | |
| — | H | O | H |
| Elion, GB & Hitchins, GH. JACS 69, 2553–2555 (1947). | | | |
| H | O | CH₃ | — |
| — | CH₃ | O | H |
| Jeong, S & Gready, JE. Biol. Chem. Hoppe Seler 373, 1139–1157 (1992). | | | |
| — | CH₃ | CH₃ | CH₂CH₂OH |
| — | H | H | CH₂CH₂OH |
| — | H | CH₃ | CH₂CH₂OH |
| — | CH₃ | H | CH₂CH₂OH |
| — | CH₃ | CH₃ | CH₃ |
| — | H | H | CH₃ |
| — | H | CH₃ | CH₃ |
| — | CH₃ | H | CH₃ |
| — | CH₃ | O | CH₂CH₂OH |
| — | H | O | CH₂CH₂OH |
| Pfleiderer, W. Chem. Ber: 107, 785–795 (1974). | | | |
| H | O | H, H | H |
| H | O | CH₃, H | H |
| H | O | H, H | CH₃ |
| H | O | CH₃, CH₃ | H |
| Argentini, M & Viscontini, M. Helv. Chim. Acta 56(8), 2920–2924 (1973). | | | |
| — | H₂ | H, H | — |
| H | CH₂NH₂CH₃ | H, CH₃ | H |
| — | CH(NH₂)CH₃, CH₃ | H, H | — |
| — | COCH₃, CH₃ | H, H | — |
| — | CH₃ | H | — |
| Pfleiderer, W. et al. Liebigs Ann. Chem. 741, 64–78 (1970). | | | |
| — | CH₃ | H | — |
| — | H | CH₃ | — |
| — | CH₂CO₂H | H | — |
| — | CH(OC₂H₅)₂ | H | — |
| — | CO₂H | H | — |
| — | H | CO₂H | — |
| — | CO₂CH₃ | H | — |
| — | H | CO₂CH₃ | — |
| — | H | CO₂C₂H₅ | — |
| Viscontini, M & Piraux, M. Helv. Chim. Acta 113, 1000–1008 (1962). | | | |
| H | NH₂ | H | H |
| H | CONH₂ | H | H |
| H | NH₂ | CONH₂ | H |
| H | O | CONH₂ | — |
| H | OH | CONH₂ | H |
| H | OH | CN | H |
| H | NH₂, H | CONH₂, H | H |
| H | OH, H | CONH₂, H | H |
| H | O | CONH₂, H | H |
| H | OH, H | H, CN | H |
| — | H | COOH | — |
| H | O | COOH | — |
| H | O | CN | — |
| Forrest, HS et al. Helv. Chim. Acta 128, 1005–1010 (1960). | | | |
| H | H, H | H, H | H |
| H | H | H | H |

-continued

| N-5 | C-6 | C-7 | N-8 |
|---|---|---|---|
| H | SO$_3$H, H | H, H | H |
| H | CN, H | H, H | H |
| — | NH$_2$ | H | — |
| — | SO$_3$H | H | — |
| — | CN | H | — |
| — | CONH$_2$ | H | — |

Purmann, R. Liebigs Ann. Chem. 546, 98–102 (1940).

| | | | |
|---|---|---|---|
| — | O | O | — |

Pfleiderer, W. Chem. Ber. 90, 2624–31 (1957).

| | | | |
|---|---|---|---|
| H | O | CONH$_2$ | — |
| H | O | COOH | — |

Taylor, EC et al. J. Org. Chem. 40(16), 2341–2347 (1975).

| | | | |
|---|---|---|---|
| — | CH$_2$OH | H | — |

Stuart, A. & Wood, HCS. J. Chem Soc., 4186 (1963).

| | | | |
|---|---|---|---|
| H | O | H, H | H |

Totter, JR. J. Biol. Chem. 154, 105 (1944).

| | | | |
|---|---|---|---|
| H | O | O | H |

Elion, GB et al. JACS 71, 741 (1949).

| | | | |
|---|---|---|---|
| H | O | O | H |
| H | O | H, H | H |

Viscontini, M. Helv. Chim. Acta 76, 586 (1957).

| | | | |
|---|---|---|---|
| H | O | O | H |

Taylor, EC et al. J. Org. Chem. 40(16), 2336–2340 (1975).

| | | | |
|---|---|---|---|
| — | CH$_2$OH | O | CH$_3$ |
| — | H | O | CH$_3$ |
| — | H | O | H |
| — | CH$_2$OH | O | H |
| — | COOH | O | H |

Storm, CB. J. Org. Chem. 36(25), 3925–27 (1971).

| | | | |
|---|---|---|---|
| — | C$_6$H$_5$ | H | — |
| — | H | C$_6$H$_5$ | — |
| — | CH$_3$ | H | — |
| — | H | CH$_3$ | — |
| — | CH$_2$OH | H | — |

Waring P. & Armarego, WLF. Eur. J. Med Chem. 22, 83–90 (1987).

| | | | |
|---|---|---|---|
| — | CH$_3$ | H | — |
| — | CH$_3$ | H, H | H |
| H | CH$_3$, H | H, H | H |
| — | H | CH$_3$ | — |
| — | H | CH$_3$, H | H |
| H | H, H | CH$_3$, H | H |
| — | CH$_2$CH$_3$ | H | — |
| — | CH$_2$CH$_3$ | H, H | H |
| H | CH$_2$CH$_3$, H | H, H | H |
| — | CH$_2$CH$_2$CH$_3$ | H | — |
| — | CH$_2$CH$_2$CH$_3$ | H, H | H |
| H | CH$_2$CH$_2$CH$_3$, H | H, H | H |
| — | n-Hexyl | H | — |
| — | n-Hexyl | H, H | H |
| H | n-Hexyl, H | H, H | H |
| — | n-Phenylethyl | H | — |
| — | n-Phenylethyl | H, H | H |
| H | n-Phenylethyl, H | H, H | H |
| — | n-Neopentyl | H | — |
| — | n-Neopentyl | H, H | H |
| H | n-Neopentyl, H | H, H | H |
| — | H | Neopentyl | — |
| — | H | Neopentyl, H | H |
| H | H, H | Neopentyl, H | H |
| — | 6R(1'R, 2'S)1, 2 Dihydroxy propyl | H | — |
| — | 6R(1'R, 2'S)1, 2 Dihydroxy propyl | H, H | H |
| H | 6R(1'R, 2'S)1, 2 Dihydroxy propyl, H | H, H | H |
| — | p-Methylaminobenzoate glutamic acid | H | — |
| — | p-Methylaminobenzoate glutamic acid | H, H | H |
| H | p-Methylaminobenzoate glutamic acid; H | H, H | H |
| — | CH$_3$, CH$_3$ | H | — |
| — | CH$_3$, CH$_3$ | H, H | H |
| H | CH$_3$, CH$_3$ | H, H | H |

Pfleiderer, W. Chem. Ber. 101, 1072–1088 (1968).

| | | | |
|---|---|---|---|
| — | H | H | CH$_3$ |
| — | CH$_3$ | CH$_3$ | CH$_3$ |
| — | C$_6$H$_5$ | C$_6$H$_5$ | CH$_3$ |
| — | CH$_3$ | H, H | H |
| — | H | OH, H | CH$_3$ |
| — | CH$_3$ | CH$_3$, OH | CH$_3$ |

Pfleiderer, W. Chem. Ber. 95, 755–62 (1962).

| | | | |
|---|---|---|---|
| — | OCH$_3$ | H | — |
| — | OC$_2$H$_5$ | H | — |
| — | OC$_3$H$_7$ | H | — |

Pfleider, W. & Mengel, R. Chem. Ber. 104, 2313–2323 (1971).

| | | | |
|---|---|---|---|
| CH$_3$ | CH$_3$ | CH$_3$, H | C$_6$H$_5$ |
| CH$_3$ | CH$_3$ | CH$_3$, H | CH$_3$ |
| — | CH$_3$ | CH$_3$, H | CH$_3$ |
| CH$_3$ | C$_6$H$_5$, OH | C$_6$H$_5$, H | CH$_3$ |

Pfleiderer, W. & Mengel, R. Chem. Ber. 104, 2293–2312 (1971).

| | | | |
|---|---|---|---|
| CHO | H, H | H, H | CH$_3$ |
| CHO | H, H | H, H | C$_6$H$_5$ |
| CHO | H, H | H, H | p-ClC$_6$H$_5$ |
| CHO | CH$_3$, H | CH$_3$, H | CH$_3$ |
| CHO | CH$_3$, H | CH$_3$, H | C$_6$H$_5$ |
| CHO | CH$_3$, H | CH$_3$, H | CH$_2$C$_6$H$_5$ |
| COCH$_3$ | CH$_3$, H | CH$_3$, H | C$_6$H$_5$ |
| COCH$_3$ | CH$_3$, H | CH$_3$, H | p-ClC$_6$H$_5$ |
| COCH$_3$ | CH$_3$, H | CH$_3$, H | CH$_2$C$_6$H$_5$ |
| CHO | C$_6$H$_5$, H | C$_6$H$_5$, H | CH$_3$ |
| — | H | H, H | CH$_3$ |
| H | H, H | H, H | CH$_3$ |
| — | H | H, H | C$_6$H$_5$ |
| — | CH$_3$ | CH$_3$, H | CH$_3$ |
| — | CH$_3$ | CH$_3$, H | C$_6$H$_5$ |
| — | C$_6$H$_5$ | C$_6$H$_5$, H | CH$_3$ |
| — | C$_6$H$_5$ | H, H | H |

Ivory, MT & Grady, J.J. Chem. Bio. (8), 349 (1993).

| | | | |
|---|---|---|---|
| — | H | CH$_3$ | CH$_3$ |
| — | H | CH$_3$ | n-propyl |
| — | H | CH$_3$ | CH$_2$CH$_2$OH |
| — | H | CH$_3$ | iso-propyl |
| — | CH$_3$ | H | CH$_3$ |
| — | CH$_3$ | H | n-propyl |
| — | CH$_3$ | H | CH$_2$CH$_2$OH |
| — | CH$_3$ | H | iso-propyl |

Viscontini, M & Weilenmann, HR; Helv. Chim. Acta 202, 1854–1862 (1959).

| | | | |
|---|---|---|---|
| H | H, OH | H, H | H |
| H | H, OH | H | — |
| H | H, SO$_3$H | H, H | H |
| — | SO$_3$H | H | — |
| H | H, R | H, H | H |
| — | R | H | — |

Waring, P. Aust. J. Chem. 41, 667–76 (1988).

| | | | |
|---|---|---|---|
| H | H, NH-p-C$_6$H$_4$CONH-CH(CO$_2$H)-CH$_2$CH$_2$CO$_2$H | H, H | H |
| H | H, CH$_3$ | H, H | H |
| H | H, CH$_2$OH | H, H | H |
| H | H, CH$_2$NH$_2$ | H, H | H |
| — | CN | H | — |

| N-5 | C-6 | C-7 | N-8 |
|---|---|---|---|
| — | $CONH_2$ | H | — |
| — | CH=NOH | H | — |
| — | $CHBr_2$ | H | — |
| Stuart, A. et al. J. Chem. Soc. (C), 285–88 (1966). | | | |
| — | H | H, H | H |
| — | $NH_2$ | H | — |
| — | $SO_3H$ | H | — |
| — | $CONH_2$ | H, H | h |
| H | H, $SCH_2CH_2OH$ | H, H | H |
| H | H, $SCH_2COOH$ | H, H | H |
| H | H, $CH(COOEt)_2$ | H, H | H |
| H | H, R (various) | H, H | H |
| Taylor, EC & Jacobi, PA; JACS 95(13), 4455–4456 (1973). | | | |
| — | H | H | O |
| — | $CH_3$ | H | O |

Many pterins are available by stock order or special order from Schircks Laboratories, Buechstrasse 10, CH-8645, Jona, Switzerland.

Formulations

Compounds of the invention are administered orally in a total daily dose of about 0.5 mg/kg/dose to about 70 mg/kg/dose, preferably from about 1.5 mg/kg/dose to about 35 mg/kg/dose. The use of time-release preparations to control the rate of release of the active ingredient may be preferred. The dose may be administered in as many divided doses as is convenient. When other methods are used (e.g. intravenous administration), compounds are administered to the affected tissue at a rate from 0.003 to 30 mg/kg/hour, preferably from 0.03 to 3.0 mg/kg/hour. Such rates are easily maintained when these compounds are intravenously administered as discussed below.

For the purposes of this invention, the compounds may be administered by a variety of means including orally, parenterally, by inhalation spray, topically, or rectally in formulations containing pharmaceutically acceptable carriers, adjuvants and vehicles. The term parenteral as used here includes subcutaneous, intravenous, intramuscular, and intraarterial injections with a variety of infusion techniques. Intraarterial and intravenous injection as used herein includes administration through catheters. Oral administration is generally preferred.

Pharmaceutical compositions containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipients which are suitable for the manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials optionally in admixture with excipients suitable for the manufacture of aqueous suspensions. Such excipients include a suspending agent, such as sodium carboxymethylcellulose, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin. Such suspensions may contain acids, bases, and preservatives.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient optionally in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents.

Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 6 to 6000 mg of active material compounded with an appropriate and convenient amount of carrier material which may vary from about 5 to about 95% of the total compositions. It is preferred that the pharmaceutical composition be prepared which provides easily measurable amounts for administration. For example, an aqueous solution intended for intravenous infusion should contain from about 2.3 to 23,000 μg of the active ingredient per milliliter of solution in order that infusion of a suitable volume at a rate of about 100 mL/hr can occur.

As noted above, formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet may be made by compression or molding, optionally with one or more accessory ingredients. Compressed tablets may be prepared by compressing in a suitable machine the active ingredient in a free flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropyl methylcellulose in varying proportions to provide the desired release profile. Tablets may optionally be provided with an enteric coating, to provide release in parts of the gut other than the stomach. This is particularly advantageous with the compounds of formula I when such compounds are susceptible to acid hydrolysis.

Formulations suitable for topical administration in the mouth include lozenges comprising the active ingredient in a flavored base, usually sucrose and acacia or tragacanth; pastilles comprising the active ingredient in an inert base such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous isotonic, sterile, pyrogen-free injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Injection solutions and suspensions may be prepared from sterile powders, granules and tablets of the kind previously described.

Preferred unit dosage formulations are those containing a daily dose or unit, daily sub-dose, or an appropriate fraction thereof, of a metal pterin complex.

It will be understood, however, that the specific dose level for any particular patient will depend on a variety of factors including the activity of the specific compound employed; the age, body weight, general health, sex and diet of the individual being treated; the time and route of administration; the rate of excretion; other drugs which have previously been administered; and the severity of the particular disease undergoing therapy, as is well understood by those skilled in the art.

The compounds of this invention and their preparation can be understood further by the examples which illustrate some of the processes by which these compounds are prepared. These examples should not however be construed as specifically limiting the invention and variations of the invention, now known or later developed, are considered to fall within the scope of the present invention as hereinafter claimed.

EXAMPLE 1

Used in Biologic Example A

Preparation (A) of $CaCl_2(pterin)_4$

Pterin (Shircks Laboratories, Jona, Switzerland, 99.8% pure) is made into two suspensions, A and B. Suspension A is 5 mM pterin in distilled water. Suspension B is 5 mM pterin and 5 mM $CaCl_2$ in distilled water prepared using $CaCl_2.2H_2O$. To make Suspension B, the appropriate amount of $CaCl_2.2H_2O$ is first dissolved in distilled water, followed by the addition of pterin powder. Suspension A is then mixed with suspension B in a ratio of 3 parts A to 1 part B. The resultant suspension, C, is 5 mM pterin and 1.25 mM $CaCl_2$ and is used directly for oral gavaging of the test mice. Mass Spectroscopy of the soluble portion of suspension C gave an $MH^{+1}=239$. There was also a minor peak at 309 [Ca(pterin)(pterin fragment C4N3H3)]. Mass Spec. of vortexed suspension showed a 365 peak, which is consistent with [Ca(pterin$^+$)(pterin)]. There were major peaks at 137, 186, 119, 162, 295, and 147. C, N, H Elemental analysis of the dry solid yielded C: 19.91, N: 18.71, which is equal to a molar ratio of $C_6N_5$ found in pterin.

EXAMPLE 2

Used in Biologic Example B

Preparation (B) of $CaCl_2(pterin)_4$

This example is a preferred method of making the metal-pterin suspension. Pterin (Shircks Laboratories, Jona, Switzerland, 99.8%pure) is made into two suspensions, A and B. Suspension A is 5 mM pterin in distilled water. Suspension B is 5 mM pterin and 5 mM $CaCl_2$ in distilled water prepared using $CaCl_2.2H_2O$. In Suspension B, both the appropriate amounts of $CaCl_2.2H_2O$ and pterin powder are added simultaneously to the distilled water. Suspension A is then mixed with suspension B in a ratio of 3 parts A to 1 part B. The resultant suspension, C, is 5 mM pterin and 1.25 mM $CaCl_2$ and is used directly for oral gavaging of the test mice.

The same methods may be used for preparing suspensions with other bivalent cations using the appropriate salts.

Examples of use of the method of the invention includes the following. It will be understood that these examples are exemplary and that the method of the invention is not limited solely to these examples.

Besides the following Examples, assays that may be useful for identifying compounds which possess antitumor activity include the following animal tumor models:

i) Animal models used by the National Institutes of Health to screen for antitumor activity described in Instruction 14 Screening Data Summary Interpretation Outline of Current Screens of the Drug Evaluation Branch, NCI; "Development of Human Tumor Xenograft Models for In vivo Evaluation of New Antitumor Drugs," D. J. Dykes, et al., *Contrib. Oncol.* Basel, Karger, 42:1–22, 1992; *Anticancer Drug Development Guide,* Ch. 6, "Human Tumor Xenograft Models in NCl Drug Development from Anticancer Drug Development Guide, pp.101–125 (Ed. B. Teicher) (Humana Press Inc., Totowa, N.J.); "In vivo Cultivation of Tumor Cells in Hollow Fibers," M. G. Hollingshead, et al. *Life Sciences* 57(2): 131–141 (1995). Of particular utility are tumor transplant models such as Swiss mice—Sarcoma 180, $B_6D_2F_1$ ($BDF_1$) mice, mice transplanted with Adenocarcinoma 755, and mice transplanted with L1210 Leukemia;

ii) Spontaneous tumor models such as: C3H/HeN-MTV+—mammary gland adenocarcinoma; C3H/HeOu—mammary gland adenocarcinoma.

In vitro human tumor cell screening may also be used to screen for effective antitumor agents of the invention. For example, the in vitro human cancer cell panel developed by NCI Cancer Drug Discovery and Development Program. M. R. Boyd, et al. *Drug Development Research* 34: 91–109 (1995); M. R. Grever, et al. Seminars in *Oncology,* 19(6): 622–638 (1992).

Anti-viral activity can be identified by using screens well known in the art. *Methods in Virology,* edited by K. Maramorosch and H. Koprowski, Vol. III (Academic Press, 1967).

EXAMPLES

Biologic

A. Antitumor Efficacy of Preparation (A) of $CaCl_2$ (Pterin)$_4$

A suspension of $CaCl_2$(pterin)$_4$, prepared in Example 1 was administered to C3H/HeN-MTV+ (mammary gland tumor virus) mice by oral gavage of 3/16 mL of 5 mM pterin in 1.25 mM $CaCl_2$ daily. This dosage is about 7 mg/kg/day.

Figure One shows the median tumor volume ("MTV") of the Control mice (N=4) and the Test mice (N=5) which were given $CaCl_2$(Pterin)$_4$ daily for eight (8) days. As can be seen from Figure One, $CaCl_2$(Pterin)$_4$ treatment strongly regresses tumor growth relative to controls.

The inventor has used this data to carry out an analysis based upon the National Cancer Institute's standard measure for determining tumor growth inhibition activity, T/C. LaRusso, P., et al. *Cancer Research* 50: 4900–4905 (1990). T/C is the ratio between the median tumor volume (MTV) of the Test group of tumor producing mice and the MTV of the Control group of mice. Briefly, this determination begins with periodic tumor measurements (average of greater and lesser diameters) by caliper, carried out in both treatment and control groups, beginning at the point when the tumors were palpable (Figure One). The median tumor volume of each group is determined, including zeros (remissions), for each day of measurement. The T/C value in percentage is an indication of antitumor effectiveness (Figure Two). A T/C equal to or less than 42% is considered significant antitumor activity. A T/C value <10% is indicative of a high degree of antitumor activity and is the level used by the National Cancer Institute to justify systematic toxicology studies preliminary to Investigational New Drug (IND) filing (termed DN-2 level activity). Approximately 39 compounds tested to date by the National Cancer Institute reach this designation.

Figure Two gives the daily Test to Control ratios (T/C) for the tumor size data given in Figure One. The A-line at 42% represents the level of activity established by the N.C.I. for "significant antitumor activity". The B-line at about 10% depicts the level representing a "high degree of antitumor activity". The suspension of Example 1, $CaCl_2$(Pterin)$_4$, demonstrates a high degree of antitumor activity after day 4. Most of the 39 compounds which currently pass the National Cancer Institute's standard for a high degree of antitumor activity are at various stages of development. Many have a high degree of associated in vivo toxicity. $CaCl_2$(Pterin)$_4$, on the other hand, appears to have no observed toxicity when consumed by the experimental mice at therapeutic dosages.

B. In Vivo Evaluation of Novel Antineoplastic Agent, CaPterin, Against Human Breast Tumor Xenograft This study evaluated the activity of the test agent, CaPterin, on human mammary tumor xenografts in mice. Athymic nude (nu/nu) female mice, age 3–4 weeks, were purchased from Harlan Spreague Dawley, Inc. (Indianapolis, Ind.). The animals were housed four per cage in sterile filter-topped cages in ventilated cage racks and Microisolator™ cages (LabProducts, DE). Upon arrival, the mice were quarantined for at least four working days before use. The animal facility is AAALAC-accredited. Temperature is maintained at 72+/−5° F. and relative humidity at 35–70%; a 12-hour light/dark cycle was used. The mice were fed sterile, autoclavable, certified Purina rodent chow ad libitum. Drinking water was acidified and autoclaved, and the source water was recirculated, deionized, UV-treated, and 5-um filtered. The water supply is analyzed quarterly for metals and trace contaminants.

MDA MB 231 breast cancer cells (5,000,000 cells in 100 uL of phosphate buffered saline) were injected subcutaneously into the right leg of female immunodeficient athymic nude mice. When the tumors reached a mean diameter of 3–5 mm, the mice were divided into two groups (8 mice per treatment group), and the treatment begun. The mice were treated by oral gavage once daily for 14 days with either 3/16 mL of the vehicle control (water) or with 3/16 mL of 5 mM $CaCl_2$ .Pterin from Example 2.

Tumor dimensions and body weights were measured 4 times weekly for approximately three weeks from the start of treatment. Tumors were measured in three planes using Vernier calipers, and tumor volume (V) was calculated as follows: V=pi(x x y x z)/6, where x, y, and z are the tumor measurements minus skin thickness. The mean tumor volume was calculated at each time point. For each group, the mean of the ratio V/Vo was plotted as a function of time after treatment, and tumor growth delay calculated. Treatment toxicity was assessed from reductions in body weight after treatment. The mice were sacrificed if their tumor volumes reached greater than or equal to 1600 mm$^3$ or weight loss exceeded 25%.

Throughout the course of treatment, no evidence of toxicity was found in any of the mice.

Figure Three shows the mean growth response as relative tumor volume of human breast xenografts in nude mice treated with CaPterin. When tumors reached 3–5 mm in diameter (day 0), test animals were treated daily with oral doses of CaPterin. As can be seen from Figure Three, CaPterin strongly regresses tumor growth relative to controls.

Figure 3:
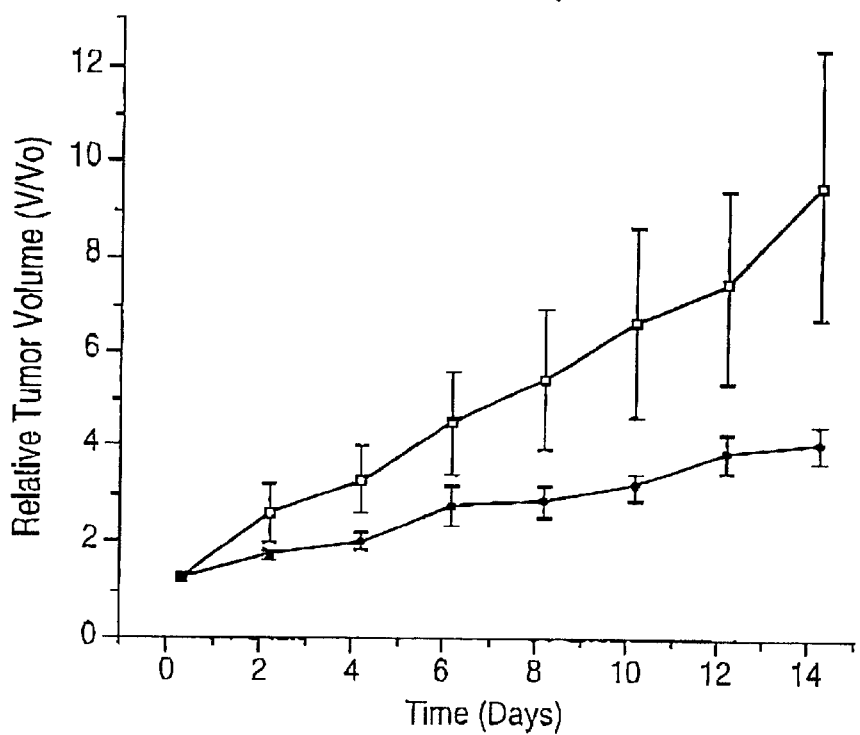
Figure 4:
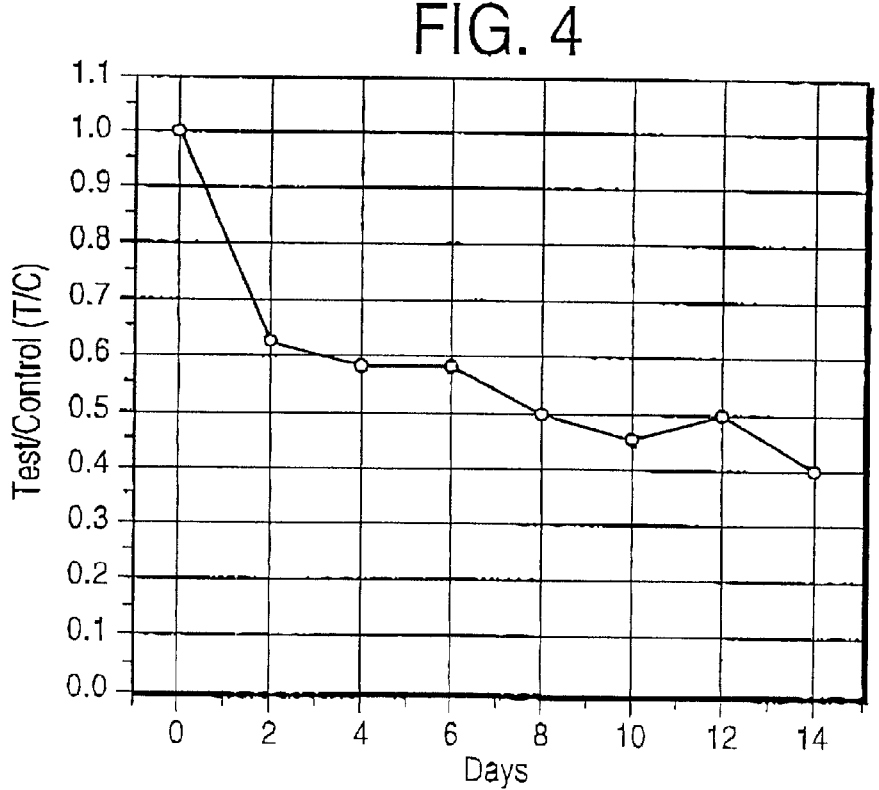

FIG. 3: Key: upper line □, control; lower line ♦, treated; Vo, mean initial volume. Error bars represent the standard error of the mean for measurement of groups of animals consisting of eight members each.

Figure Four gives the daily tumor volume ratio of test mice (V/Vo) to control mice, the test to control ratio (T/C), with a T/C<42% at Day 14.

As discussed above in Example A, the T/C ratio is an indication of antitumor effectiveness. The National Cancer Institute criteria for significant antitumor activity is T/C= 42%. Figures Three and Four show that the orally administered test complex of CaPterin surpasses this criteria with a T/C ratio of less than or equal to 42%.

I claim:

1. A compound of formula (I):

wherein:
M is a bivalent metal ion selected from the group consisting of $Ca^{2+}$, $Cu^{2+}$, $Mg^{2+}$, $V^{2+}$, $Cr^{2+}$, $Mn^{2+}$, $Fe^{2+}$, $Mo^{2+}$, $Zn^{2+}$, $Sr^{2+}$, $Ba^{2+}$, $Ra^{2+}$, $Ru^{2+}$, $Rh^{2+}$, $Pd^{2+}$, $Cd^{2+}$, $Sn^{2+}$, $W^{2+}$, $Re^{2+}$, $Os^{2+}$, $Ir^{2+}$, $Pt^{2+}$, $Si^{2+}$, and $Sm^{2+}$;

X is an anion of an acid and has a charge of −1 or −2 when ionized;

a is an integer of from 1 to 2;

y is an integer of from 1 to 6; and z is an integer of from 1 to 6;

with the provisos that a) when M is $Cu^{2+}$, then Pterin is not pterin, or 6-carboxypterin;

b) when M is $Ca^{2+}$, then Pterin is not xanthopterin, isoxanthopterin, or neopterin; and c) when M is $Zn^{2+}$, then Pterin is not pterin.

2. The compounds of claim 1 wherein M is a bivalent metal ion selected from the group consisting $Sr^{2+}$, $Ba^{2+}$, $Ra^{2+}$, $Ru^{2+}$, $Rh^{2+}$, $W^{2+}$, $Re^{2+}$, $Os^{2+}$, $Ir^{2+}$, $Pt^{2+}$, $Pd^{2+}$, $Cd^{2+}$, $Sn^{2+}$, $Si^{2+}$, and $Sm^{2+}$.

3. The compound of claim 1 wherein M is a bivalent metal ion selected from the group consisting of $Ca^{2+}$, $Cu^{2+}$, $Mg^{2+}$, $V^{2+}$, $Cr^{2+}$, $Mn^{2+}$, $Fe^{2+}$, $Mo^{2+}$, and $Zn^{2+}$.

4. The compounds of claim 3 wherein a is 1 or 2.

5. The compounds of claim 3 wherein M is selected from the group consisting of $Ca^{2+}$, $Cu^{2+}$, $Mg^{2+}$, $V^{2+}$, $Cr^{2+}$, $Mn^{2+}$, $Fe^{2+}$, and $Mo^{2+}$.

6. The compounds of claim 5 wherein M is selected from the group consisting of $Ca^{2+}$ and $Cu^{2+}$.

7. The compounds of claim 3 wherein each X is independently selected from the group consisting of F$^-$, Cl$^-$, Br$^-$, I$^-$, RCOO$^-$, $CO_3^{2-}$, $HPO_3^{2-}$, $SO_4^{2-}$, and $SO_3^-$.

8. The compounds of claim 7 wherein X is selected from the group consisting of F$^-$, Cl$^-$ and Br$^-$.

9. The compounds of claim 3 wherein y is 1 and z is 2.

10. The compounds of claim 3 wherein y is 1 and z is 4.

11. The compounds of claim 3 wherein
M is selected from the group consisting of $Ca^{2+}$ and $Cu^{2+}$; and
X is selected from the group consisting of F$^-$, Cl$^-$ and Br$^-$.

12. The compounds of claim 3 that are selected from the group consisting of $CaX_2(Pterins)_2$, $CuX_2(Pterins)_2$, $CaX_2(Pterins)_4$, and $CuX_2(Pterins)_4$.

13. The compounds of claim 12 wherein in said Pterins is pterin.

14. The compounds of claim 12 wherein X is selected from the group consisting of F$^-$, Cl$^-$ and Br$^-$.

15. A method of inhibiting tumor cells in an animal comprising the administration of a therapeutically effective amount of a compound of formula (I):

wherein:
M is a bivalent metal ion selected from the group consisting of $Ca^{2+}$, $Cu^{2+}$, $Mg^{2+}$, $V^{2+}$, $Cr^{2+}$, $Mn^{2+}$, $Fe^{2+}$, $Co^{2+}$, $Mo^{2+}$, $Zn^{2+}$, $Sr^{2+}$, $Ba^{2+}$, $Ra^{2+}$, $Ru^{2+}$, $Rh^{2+}$, $Pd^{2+}$, $Cd^{2+}$, $Sn^{2+}$, $W^{2+}$, $Re^{2+}$, $Os^{2+}$, $Ir^{2+}$, $Pt^{2+}$, $Si^{2+}$, and $Sm^{2+}$;

X is an anion of an acid and has a charge of −1 or −2 when ionized;

a is an integer of from 1 to 2;

y is an integer of from 1 to 6; and z is an integer of from 1 to 6;

with the provisos that a) when M is $Cu^{2+}$, then Pterin is not pterin, or 6-carboxypterin;

b) when M is $Ca^{2+}$, then Pterin is not xanthopterin, isoxanthopterin, or neopterin; and c) when M is $Zn^{2+}$, then Pterin is not pterin.

16. A method of treating a viral infection comprising the administration of a therapeutically effective amount of a compound of formula (I):

wherein:
M is a bivalent metal ion selected from the group consisting of $Ca^{2+}$, $Cu^{2+}$, $Mg^{2+}$, $V^{2+}$, $Cr^{2+}$, $Mn^{2+}$, $Fe^{2+}$, $Co^{2+}$, $Mo^{2+}$, $Zn^{2+}$, $Sr^{2+}$, $Ba^{2+}$, $Ra^{2+}$, $Ru^{2+}$, $Rh^{2+}$, $Pd^{2+}$, $Cd^{2+}$, $Sn^{2+}$, $W^{2+}$, $Re^{2+}$, $Os^{2+}$, $Ir^{2+}$, $Pt^{2+}$, $Si^{2+}$, and $Sm^{2+}$.

X is an anion of an acid and has a charge of −1 or −2 when ionized;

a is an integer of from 1 to 2;

y is an integer of from I to 6; and z is an integer of from 1 to 6;

with the provisos that a) when M is $Cu^{2+}$, then Pterin is not pterin, or 6-carboxypterin;

b) when M is $Ca^{2+}$, then Pterin is not xanthopterin, isoxanthopterin, or neopterin; and c) when M is $Zn^{2+}$, then Pterin is not pterin.

17. A method of treating animal malignant tumor cells, which comprises administering to an animal affected with said tumor cells a suspension made from a mixture of Pterins, a salt of a bivalent cation selected from the group consisting of $Ca^{2+}$, $Cu^{2+}$, $Mg^{2+}$, $V^{2+}$, $Cr^{2+}$, $Mn^{2+}$, $Fe^{2+}$, $Co^{2+}$, $Mo^{2+}$, $Zn^{2+}$, $Sr^{2+}$, $Ba^{2+}$, $Ra^{2+}$, $Ru^{2+}$, $Rh^{2+}$, $Pd^{2+}$, $Cd^{2+}$, $Sn^{2+}$, $W^{2+}$, $Re^{2+}$, $Os^{2+}$, $Ir^{2+}$, $Pt^{2+}$, $Si^{2+}$, and $Sm^{2+}$, and optionally pharmaceutically acceptable acids, bases, and excipients, in a mole ratio of Pterins: salt of a bivalent cation of from about 1:1 to about 4:1;

with the provisos that
 a) when M is $Cu^{2+}$, then Pterin is not pterin, or 6-carboxypterin;
 b) when M is $Ca^{2+}$, then Pterin is not xanthopterin, isoxanthopterin, or neopterin; and
 c) when M is $Zn^{2+}$, then Pterin is not pterin.

18. The methods of claim 17 wherein said bivalent cation is selected from the group consisting of $Ca^{2+}$, $Cu^{2+}$, $Mg^{2+}$, $V^{2+}$, $Cr^{2+}$, $Mn^{2+}$, $Fe^{2+}$, $Co^{2+}$, $MO^{2+}$ and $Zn^{2+}$.

19. The methods of claim 17 wherein the bivalent cation is selected from the group consisting of $Sr^{2+}$, $Ba^{2+}$, $Ra^{2+}$, $Ru^{2+}$, $Rh^{2+}$, $W^{2+}$, $Re^{2+}$, $Os^{2+}$, $Ir^{2+}$, $Pt^{2+}$, $Pd^{2+}Cd^{2+}$, $Sn^{2+}$, $Si^{2+}$, and $Sm^{2+}$.

20. The methods of claim 18 wherein said bivalent cation is selected from the group consisting of $Ca^{2+}$, $Cu^{2+}$, $Mg^{2+}$, $V^{2+}$, $Cr^{2+}$, $Mn^{2+}$, $Fe^{2+}$, $Co^{2+}$, and $Mo^{2+}$.

21. The methods of claim 20 wherein said salt is selected from the group consisting of $CaCl_2$, and $CuCl_2$.

22. The methods of claim 21 wherein said mole ratio of Pterins: salt is about 4:1.

23. The methods of claim 22 wherein said Pterins is pterin.

24. A composition prepared by mixing Pterins, a salt of a bivalent cation selected from the group consisting of $Ca^{2+}$, $Cu^{2+}$, $Mg^{2+}$, $V^{2+}$, $Cr^{2+}$, $Mn^{2+}$, $Fe^{2+}$, $Mo^{2+}$, $Zn^{2+}$, $Sr^{2+}$, $Ba^{2+}$, $Ra^{2+}$, $Ru^{2+}$, $Rh^{2+}$, $Pd^{2+}$, $Cd^{2+}$, $Sn^{2+}$, $W^{2+}$, $Re^{2+}$, $Os^{2+}$, $Ir^{2+}$, $Pt^{2+}$, $Si^{2+}$, and $Sm^{2+}$, and a polar solvent;

with the provisos that
 a) when M is $Cu^{2+}$, then Pterin is not pterin, or 6-carboxypterin;
 b) when M is $Ca^{2+}$, then Pterin is not xanthopterin, isoxanthopterin, or neopterin; and
 c) when M is $Zn^{2+}$, then Pterin is not pterin.

25. The compositions of claim 24 wherein said bivalent cation is selected from the group consisting of $Ca^{2+}$, $Cu^{2+}$, $Mg^{2+}$, $V^{2+}$, $Cr^{2+}$, $Mn^{2+}$, $Fe^{2+}$, $Mo^{2+}$, and $Zn^{2+}$.

26. The compositions of claim 25 wherein said Pterin is pterin.

27. The compositions of claim 26 wherein said polar solvent is selected from the group consisting of water, saline, buffer, DMSO, ethanol, and isopropyl alcohol.

28. The composition of claim 26 further comprising a pharmaceutically acceptable acid, base, salt or excipient.

29. The composition of claim 26 that is a suspension.

30. A pharmaceutical composition comprising a pharmaceutically acceptable excipient and a compound of formula (I):

$$(MX_a)_y(Pterins)_z \qquad (I)$$

wherein:
 M is a bivalent metal ion selected from the group consisting of $Ca^{2+}$, $Cu^{2+}$, $Mg^{2+}$, $V^{2+}$, $Cr^{2+}$, $Mn^{2+}$, $Fe^{2+}$, $Co^{2+}$, $Mo^{2+}$, $Zn^{2+}$, $Sr^{2+}$, $Ba^{2+}$, $Ra^{2+}$, $Ru^{2+}$, $Rh^{2+}$, $Pd^{2+}$, $Cd^{2+}$, $Sn^{2+}$, $W^{2+}$, $Re^{2+}$, $Os^{2+}$, $Ir^{2+}$, $Pt^{2+}$, $Si^{2+}$, and $Sm^{2+}$;
 X is an anion of an acid and has a charge of $-1$ or $-2$ when ionized;
 a is an integer of from 1 to 2;
 y is an integer of from 1 to 6; and
 z is an integer of from 1 to 6;
 with the provisos that
 a) when M is $Cu^{2+}$, then Pterin is not pterin, or 6-carboxypterin;
 b) when M is $Ca^{2+}$, then Pterin is not xanthopterin, isoxanthopterin, or neopterin; and
 c) when M is $Zn^{2+}$, then Pterin is not pterin.

31. The pharmaceutical composition of claim 30 wherein M is a bivalent metal ion selected from the group consisting of $Sr^{2+}$, $Ba^{2+}$, $Ra^{2+}$, $Ru^{2+}$, $Rh^{2+}$, $W^{2+}$, $Re^{2+}$, $Os^{2+}$, $Ir^{2+}$, $Pt^{2+}$, $Pd^{2+}$, $Cd^{2+}$, $Sn^{2+}$, $Si^{2+}$, and $Sm^{2+}$.

32. The pharmaceutical composition of claim 30 wherein M is a bivalent metal ion selected from the group consisting of $Ca^{2+}$, $Cu^{2+}$, $Mg^{2+}$, $V^{2+}$, $Cr^{2+}$, $Mn^{2+}$, $Fe^{2+}$, $Co^{2+}$, $Mo^{2+}$, and $Zn^{2+}$.

33. The pharmaceutical composition of claim 32 wherein a is 1 or 2.

34. The pharmaceutical composition of claim 32 wherein M is selected from the group consisting of $Ca^{2+}$, $Cu^{2+}$, $Mg^{2+}$, $V^{2+}$, $Cr^{2+}$, $Mn^{2+}$, $Fe^{2+}$, $Co^{2+}$, and $Mo^{2+}$.

35. The pharmaceutical composition of claim 34 wherein M is selected from the group consisting of $Ca^{2+}$ and $Cu^{2+}$.

\* \* \* \* \*